(12) United States Patent
Proksch (10) Patent No.: US 7,066,005 B2
(45) Date of Patent: *Jun. 27, 2006

(54) NONCONTACT SENSITIVITY AND COMPLIANCE CALIBRATION METHOD FOR CANTILEVER-BASED INSTURMENTS

(75) Inventor: Roger Proksch, Santa Barbara, CA (US)

(73) Assignee: Asylum Research Corporation, Santa Barbara, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 190 days.

(21) Appl. No.: 10/087,196

(22) Filed: Feb. 28, 2002

(65) Prior Publication Data

US 2002/0162388 A1 Nov. 7, 2002

Related U.S. Application Data

(60) Provisional application No. 60/272,697, filed on Feb. 28, 2001.

(51) Int. Cl.
*G01B 21/30* (2006.01)
*G01B 21/00* (2006.01)
*G01B 11/00* (2006.01)

(52) U.S. Cl. ......................................... 73/1.79; 73/1.89
(58) Field of Classification Search ................ 702/116, 702/150, 56, 42; 73/579, 105, 1.89, 1.79; 356/614; 250/252.1
See application file for complete search history.

(56) References Cited

U.S. PATENT DOCUMENTS

| | | | | |
|---|---|---|---|---|
| 4,771,237 A * | 9/1988 | Daley | ...................... | 73/1.79 X |
| 5,978,743 A * | 11/1999 | Kiyono | ....................... | 702/80 |
| 6,142,006 A * | 11/2000 | Marchon et al. | ......... | 73/1.89 X |
| 6,567,752 B1* | 5/2003 | Cusumano et al. | ..... | 702/116 X |
| 6,853,187 B1* | 2/2005 | Fainchtein | ................... | 324/300 |
| 6,958,816 B1* | 10/2005 | Dogariu et al. | ............. | 356/479 |
| 2002/0152795 A1* | 10/2002 | Guerra-Vela et al. | ........ | 73/1.89 |

* cited by examiner

*Primary Examiner*—Thomas P. Noland
(74) *Attorney, Agent, or Firm*—Morgan, Lewis & Bockius LLP (57) ABSTRACT

A method for determining physical properties of micromachined cantilevers used in cantilever-based instruments, including atomic force microscopes, molecular force probe instruments and chemical or biological sensing probes. The properties that may be so determined include optical lever sensitivity, cantilever spring constant and cantilever-sample separation. Cantilevers characterized with the method may be used to determine fluid flow rates. The method is based on measurements of cantilever deflection resulting from drag force as the cantilever is moved through fluid. Unlike other methods for determining such physical properties of cantilevers, the method described does not depend on cantilever contact with a well-defined rigid surface. Consequently, the method may be employed in situations where such contact is undesirable or inconvenient. The method has numerous applications, including molecular force measurements, atomic force microscopy and manipulation technology, chemical or biological sensing, [lithographic manufacturing, nanometer scale surface profiling] and other aspects of nanotechnology.

8 Claims, 8 Drawing Sheets

NONCONTACT SENSITIVITY AND COMPLIANCE CALIBRATION METHOD FOR CANTILEVER-BASED INSTURMENTS

CROSS-REFERENCE TO RELATED APPLICATIONS

This application claims priority of U.S. Provisional Application No. 60/272,697, filed on Feb. 28, 2001, the disclosures of which are incorporated fully herein by reference.

REFERENCES CITED

Other Publications

Cleveland, J. P.; Manne, S.; Bocek, D.; Hansma, P. K. *Rev. Sci. Instrum.* 1993, 64.
Walters, D. A.; Cleveland, J. P.; Thomson, N. H.; Hansma, P. K.; Wendman, M. A.; Gurley, G.; Elings, V. *Rev. Sci. Instrum.* 1996, 67, 3583–3590.
T. J. Senden and W. A. Ducker, *Langmuir* 1994, 10, 1003–1004.
C. J. Drummond and T. J. Senden, *Mater. Sci. Forum* 1995, 189–190, 107–114.
Ogletree, D. F.; Carpick, R. W.; Salmeron, M. *Rev. Sci. Instrum.* 1996, 67, 3298–3306.
Sader, J. E.; Larson, I.; Mulvaney, P.; White, L. R. *Rev. Sci. Instrum.* 1995, 66, 3789–3798.
Sader, J. E. *J. Appl. Phys.* 1998, 84, 64–76.
Neumeister, J. M.; Ducker, W. A. *Rev. Sci. Instrum.* 1994, 65, 2527–31.
Scholl, D.; Everson, M. P.; Jaklevic, R. C. *Rev. Sci. Instrum.* 1994, 65, 2255–2257.
Gibson, C. T.; Watson, G. S.; Myhra, S. *Nanotechnology* 1996, 7, 259–262.
Butt, H. -J.; Siedle, P.; Seifert, K.; Fendler, K.; Seeger, T.; Bamberg, E.; Weisenhorn, A. L.; Goldie, K.; Engel, A. *J. Microsc.* 1993, 169,75–84.
Torii, A.; Sasaki, M.; Hane, K.; Okuma, S. *Meas. Sci. Technol.* 1996, 7, 179–184.
Hutter, J. L.; Bechhoefer, J. *Rev. Sci. Instrum.* 1993, 64, 1868–1873.
Butt, H. -J.; Jaschke, M. *Nanotechnology* 1995, 6, 1–7.
Miyatani, T.; Fujihara, M. *J. Appl. Phys.* 1997, 81, 7099–7115.
Sader, J. E.; Chon, J. W. M.; Mulvaney, P. *Rev. Sci. Instrum.* 1999, 70, 3967.
Landau, L. D. and Lifschitz, E. M. *Fluid Mechanics* Pergamon Press (1976).

BACKGROUND OF THE INVENTION

The present invention relates generally to methods for determining physical properties of micromachined cantilevers used in cantilever-based instruments, including atomic force microscopes, molecular force probe instruments and chemical or biological sensing probes. It also involves using cantilevers characterized with such methods to measure fluid flow rates.

Calibrating the sensitivity of cantilevers used in cantilever-based instruments is critical for correctly interpreting the results obtained from such instruments. The foundation of this calibration is the determination of the optical sensitivity of the cantilever, the relationship between deflection of the cantilever and movement of the tip of the cantilever in the z direction. For this purpose, deflection of the cantilever is measured with the optical detection means common in such instruments, a position sensor collecting light reflected off the back of the cantilever. Knowing the optical sensitivity of the cantilever, the spring constant of the cantilever may be readily calculated.

The conventional methods for determining optical lever sensitivity have either been destructive or required that the lever be brought into hard contact with a well-defined rigid surface. Because the distances are typically less than one micron, and the relative positions of the cantilever tip and such a surface difficult to locate, making such contact is far from a trivial proposition. The difficulty of the procedure is enhanced by the fact that slippage of the tip laterally over the surface introduces serious errors.

Even if the conventional methods were easy of execution, there are many instances when it is not desirable or convenient to measure optical lever sensitivity by touching a surface. When the results depend on chemical or biological sensitization of the cantilever tip, or if the tip is particularly sharp, hard contact or any contact before performing the experiment may compromise the results. Similarly compromising may be hard contact when the sample is coated on the surface and is a soft material such as cells. Finally, in the case of chemical or biological sensing probes, there may not be a rigid surface anywhere near the cantilever against which to press.

Two methods for determining optical lever sensitivity not requiring hard contact with a well-defined rigid surface have been proposed, but each has important limitations and is as yet untested. D'Costa and Hoh proposed estimation of optical lever sensitivity by moving the spot across the position sensor a known distance. Because it is not sensitive to actual motion of the cantilever, this method does not account for differences in cantilever geometry or changes in the alignment of the spot on the lever. These issues become even more critical as the length scale of cantilevers shrink. Sader proposes to rely on a plan view of the lever and the measured resonant frequency and quality factor to estimate optical lever sensitivity spring constant.

Although there has been a large amount of work dedicated to the cantilever calibration issue, the precision of the resulting techniques seems to be limited to 10%. In this situation, it is desirable to make use of another method to check for consistency.

SUMMARY OF THE INVENTION

An object of the present invention is to provide a simple method for calibrating the sensitivity of any type of cantilever used in cantilever-based instruments without making contact with any surface.

A second object is to provide a method for the cantilever to approach a sample surface in a gentle and repeatable manner.

Another objective is to provide a method for calibrating the sensitivity of cantilevers that is easily automated.

Another objective is to measure fluid flow rates using micromachined cantilevers.

These and other objects are achieved according to the present invention by (i) measuring the deflection of the cantilever as it moves at a measured velocity through a fluid, (ii) determining the resonant frequency and quality factor of the cantilever by measuring its thermal spectrum and (iii) deriving optical lever sensitivity from combining these measurements.

DESCRIPTION OF THE PREFERRED EMBODIMENTS

Figure 1:
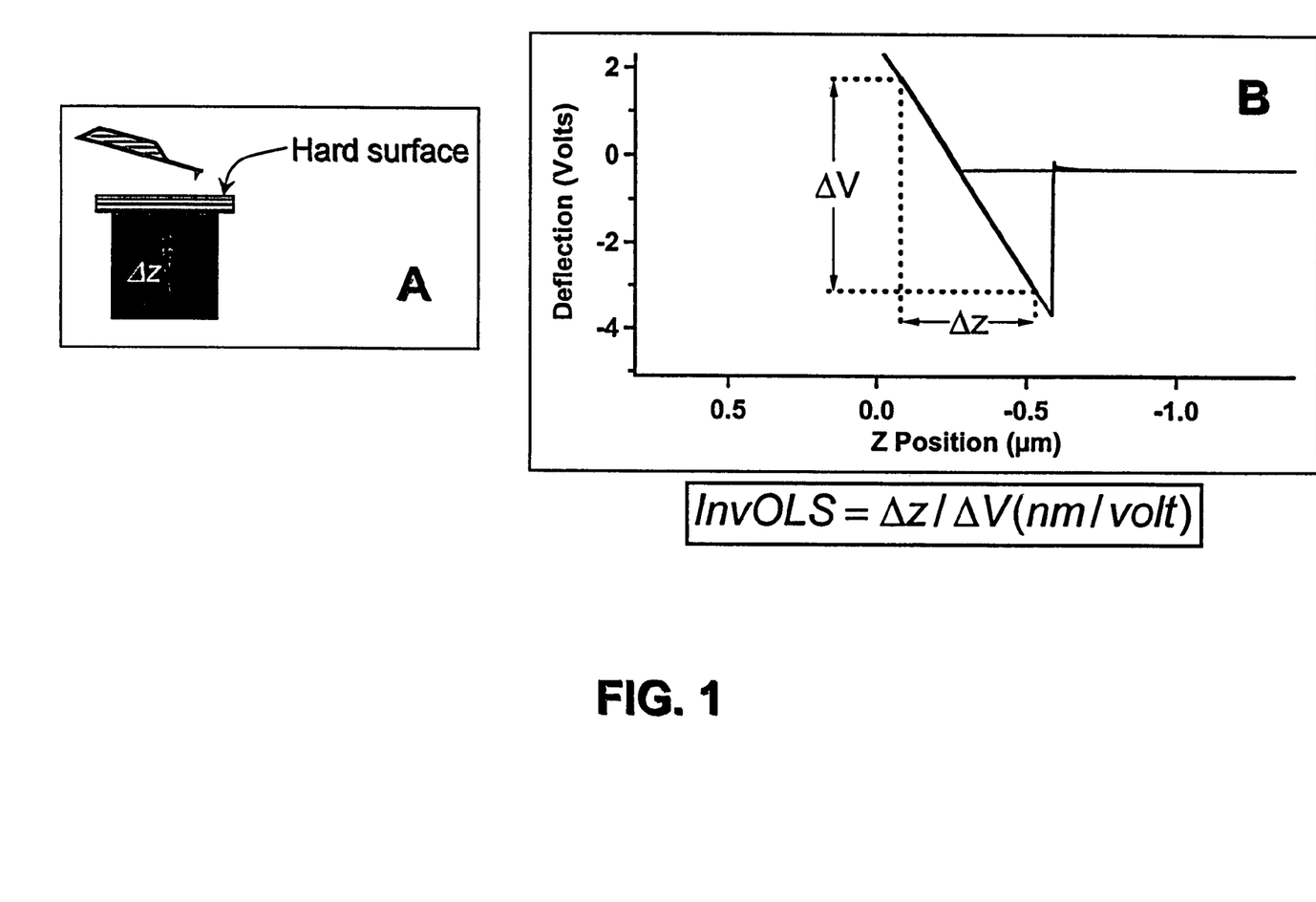
FIG. 1A depicts a simplified plane view of cantilever to be placed in contact with a hard surface for calculating optical lever sensitivity according to previous methods.
FIG. 1B shows a graphical representation of cantilever deflection in relation to a distance (Z) between the cantilever and the surface of FIG. 1A.

The optical sensitivity of the micromachined cantilever, the derivative of the change in cantilever deflection with respect to change in the z position of the cantilever tip (typically abbreviated as "OLS"), is the foundation for correctly interpreting the results obtained from cantilever-based instruments. FIG. 1A depicts one of the conventional methods for determining OLS. As shown in the panel, the cantilever is pressed into a hard surface (typically freshly cleaved mica) by the instrument (not shown) and moved an arbitrary distance measured by the instrument. Deflection of the cantilever resulting from this change in position is measured with optical detection means commonly employed in such instruments: low coherence light is focused onto the back of the cantilever with an adjustable focus lens and the light reflecting off the cantilever is collected by an adjustable mirror and guided onto position sensor. The position sensor provides a voltage that is proportional to the deflection of the cantilever.

FIG. 1B shows a graphical representation of the deflection of the cantilever vs. the z position of the tip. As shown in FIG. 1B, it is typical to calculate optical sensitivity as the inverse of OLS ("InvOLS"), the derivative of change in the z position of the cantilever tip with respect to change in cantilever deflection.

Knowing InvOLS permits us to calculate the cantilever spring constant, k, from the Equipartition of Energy Theorem:

$$\frac{1}{2}k_B T = \frac{1}{2}k \langle A^2 \rangle \quad (1)$$

where $k_B$ is Boltzmann's constant, T is the temperature, k is the cantilever spring constant and $\langle A^2 \rangle$ is the mean squared cantilever amplitude ($\langle A^2 \rangle = \text{InvOLS}^2 \cdot \Delta V^2$, where $\Delta V$ is cantilever deflection in volts).

As previously noted, it is not always desirable or convenient to determine InvOLS by making hard contact with a well-defined rigid surface as shown in FIG. 1A. The invention disclosed here permits determination of InvOLS without touching a surface by measuring cantilever deflection resulting from drag force as the cantilever is moved through a fluid (including air).

Figure 2:
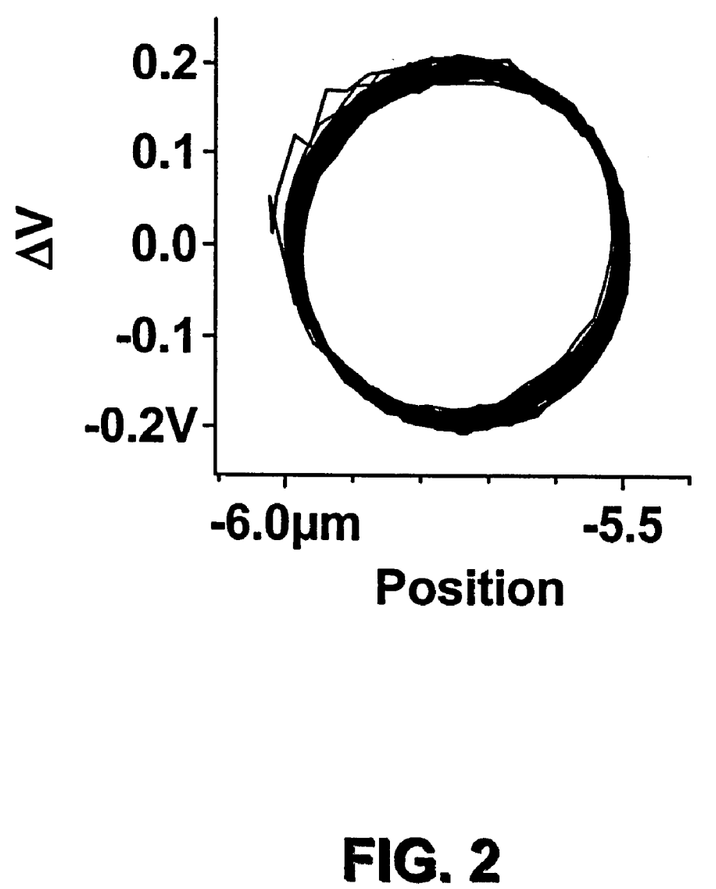
FIG. 2 depicts a graphical representation of a measured hysteresis of deflection resulting from oscillating a cantilever.

A cantilever moving through a fluid will be deflected by a viscous drag force. The measured cantilever deflection is converted to a force using $F_{hyst} = k \cdot \text{InvOLS} \cdot \Delta V$, where $\Delta V$ is cantilever deflection in volts as measured by the position sensor. If the cantilever is moving at a speed v through the fluid, we can characterize the dissipative force, which absent turbulence is equal to the drag force, as $F_{hyst} = -b_{hyst} v$, with $b_{hyst}$ being the damping coefficient. FIG. 2 shows a typical hysteresis loop measured by a 40 Hz sinusoidal cycling of the base position of a cantilever while monitoring cantilever deflection with a position sensor.

An independent measurement of the damping coefficient can be made by observing the thermal fluctuations of the cantilever. The simple harmonic oscillator model gives the damping coefficient in terms of the spring constant k, the resonant frequency $\omega_0$ and the quality factor Q as;

$$b_{therm} = \frac{k}{\omega_0 Q} \quad (2)$$

Figure 3:
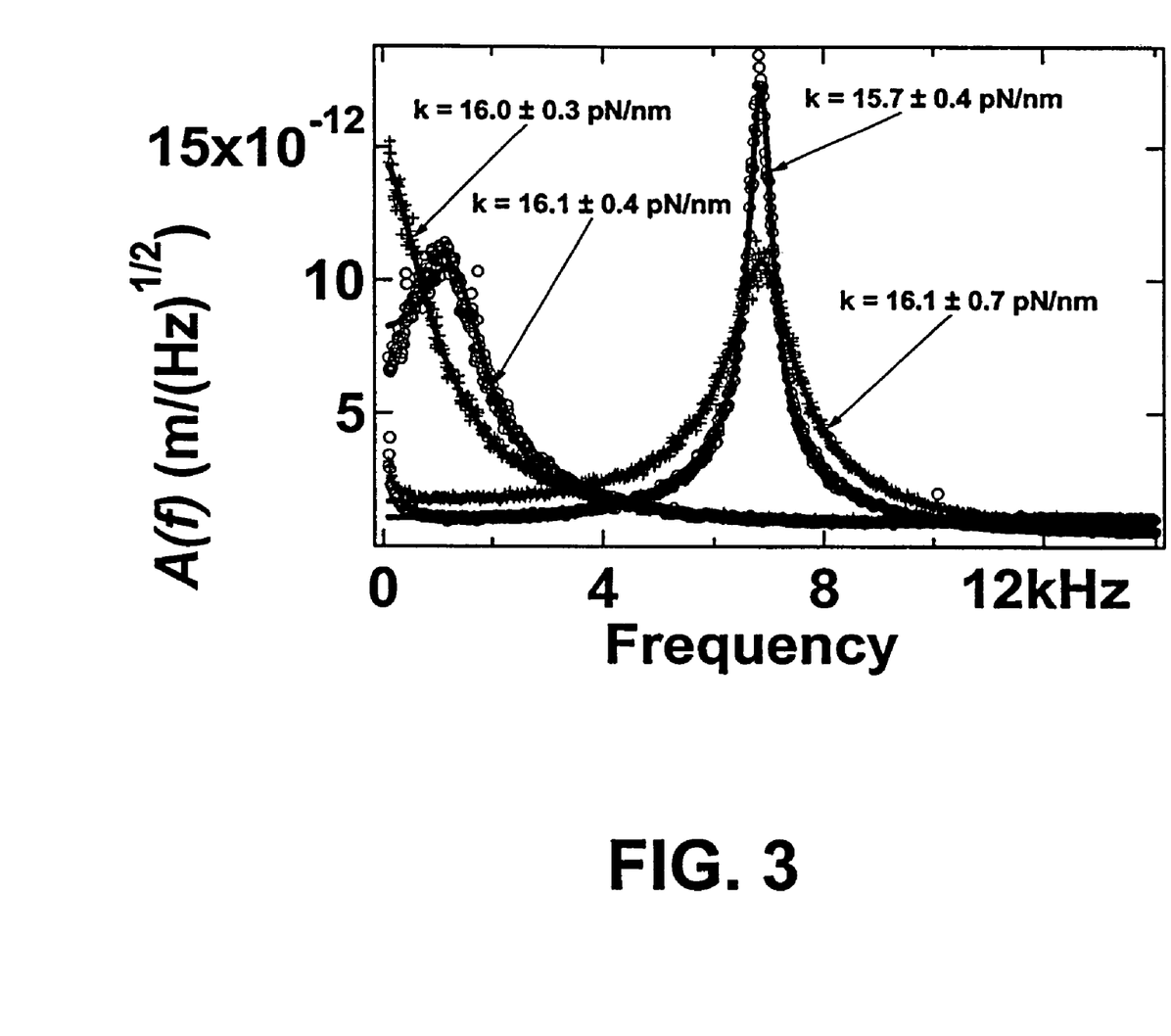
FIG. 3 depicts a graphical representation of a power spectrum for a plurality of cantilevers exposed to various environmental conditions during oscillation of the cantilever.

FIG. 3 shows four power spectra of cantilevers in fluid. The two high frequency curves 350, 352 were made in air, where a first measurement depicted by the first curve 350 was performed with the cantilever relatively far away from the surface, and the second measurement depicted by the second curve 352 was performed with the cantilever relatively close to the surface. The second spectrum 352 taken close to the surface had increased damping, yielding a peak with a lower quality factor. The third and fourth curves 354, 356 with low peak frequencies were taken in fluid, which caused the resonance to be significantly damped. The fluid is also carried along with the lever as it moves, creating an effective mass that lowers the resonant frequency. The measured spring constants of the four levers (using the method of Flutter and Bechoefer, which requires hard contact with a surface) are virtually the same despite the different environments.

From the data derived from the calculation of such power spectra, and using Equation 2, the damping coefficient, $b_{therm}$, may be calculated. In some embodiments, the power spectra is calculated through a computer means, such as a computer or processor.

As is well known (see for example, Landau and Lifschitz, *Fluid Mechanics*), damping is a complicated function of the geometry of the damped system, fluid properties and the amplitude and frequency of the motion. However, for micromachined cantilevers in cantilever-based instruments, we have found experimentally that the thermal and hysteretic damping coefficients are related by $b_{hyst} = \kappa \cdot b_{therm}$, where $\kappa$ is a phenomenological factor that depends on the fluid properties, drive frequency, tip-sample separation and the specific lever geometry. This relationship between the thermal and hysteretic damping coefficients allows us to combine the expressions for viscous drag force and dissipative force in an expression for InvOLS, all in terms of variables measured away from a surface:

$$InvOLS_{hyst} = \frac{\kappa v}{\omega_0 Q \Delta V}. \tag{3}$$

Once $InvOLS_{hyst}$ has been determined, the spring constant can be calculated from the rearranged Equipartition of Energy Theorem:

$$k = \frac{k_B T}{InvOLS^2 \Delta V^2}. \tag{4}$$

Figure 4:
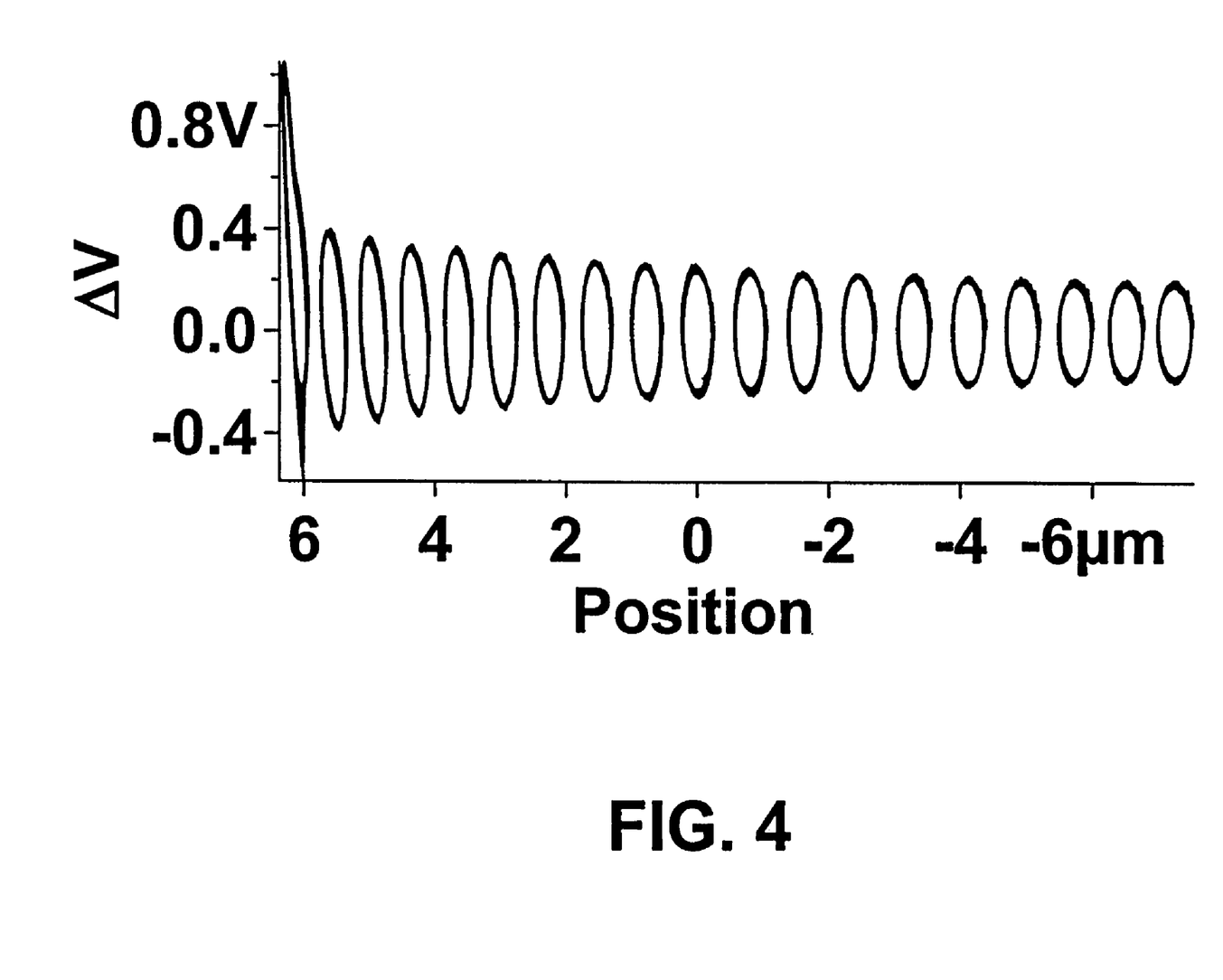
FIG. 4 depicts a graphical representation of a plurality of measured hysteresis loops as a cantilever base is moved relative to a surface.
Figure 5:
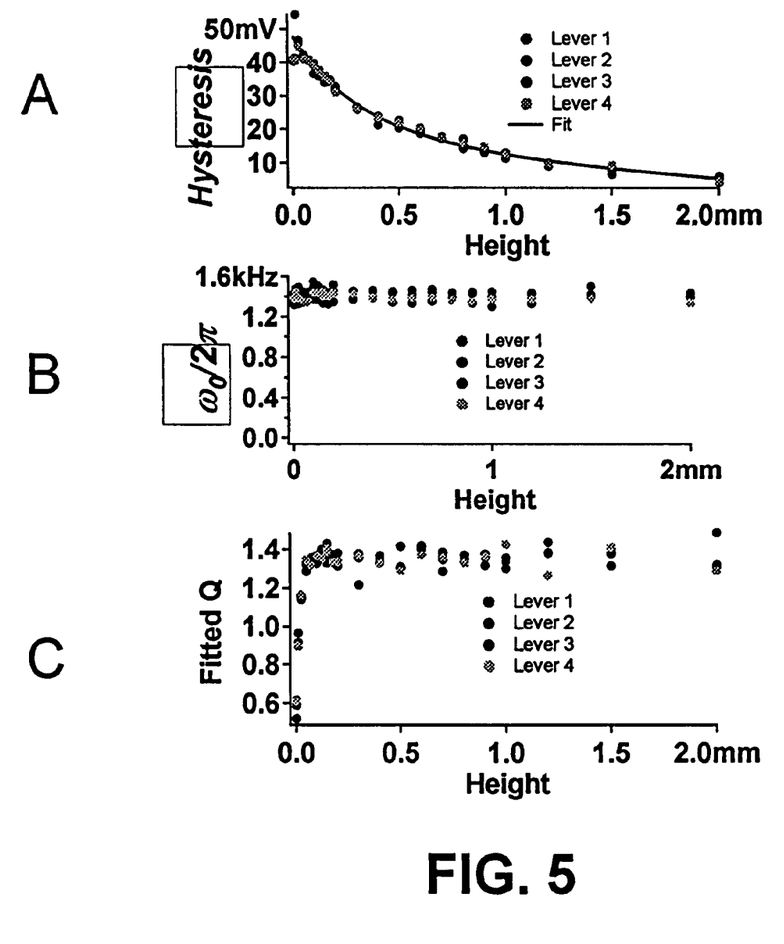
FIG. 5A depicts a graphical representation of the amplitude of hysteretic damping as a function of cantilever tip separation from a surface for a plurality of cantilevers over a range of cantilever base excitation amplitudes and frequencies.
FIG. 5B depicts a graphical representation of a resonant frequency measured with thermal noise as a function of the tip sample separation for a series of cantilevers.
FIG. 5C depicts a graphical representation of a quality factor as a function of tip sample separation for a plurality of cantilevers.
Figure 6:
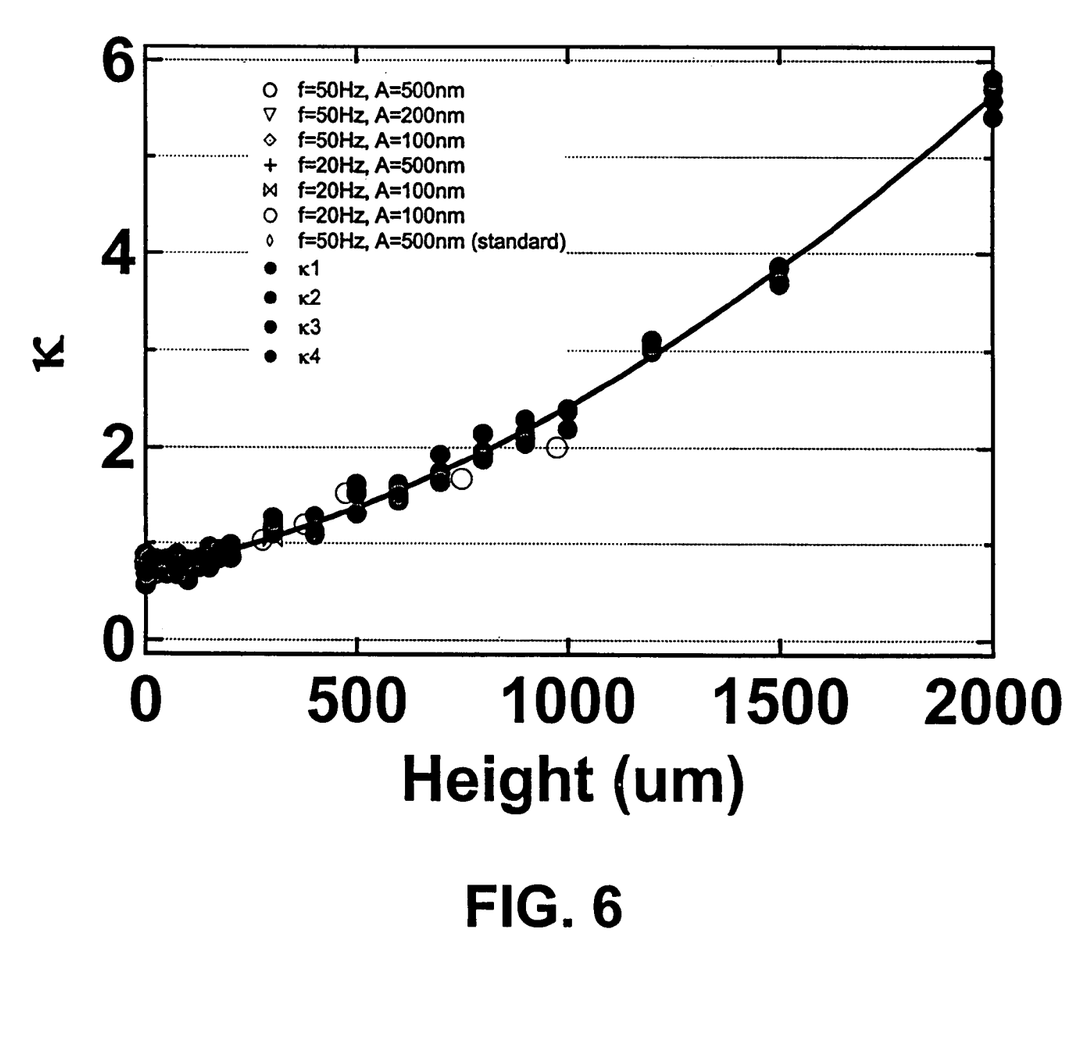
FIG. 6 depicts a graphical representation of a phenomenological factor as a function of cantilever tip separation from a surface for a plurality of different amplitudes, frequencies and cantilevers.

FIG. 4 shows a series of hysteresis loops measured at different cantilever tip-sample separations ($\Delta Z$). It is shown that measurements taken as the tip of the cantilever approaches the surface (towards the left of the Figure), the damping increases, until, in the last loop, intermittent contact with the surface is made. FIG. 5A shows the amplitude of the hysteretic damping as a function of tip-sample separation for a range of cantilever base excitation amplitudes and frequencies. These data were extracted from a number of measurements similar to those shown in FIG. 4. FIG. 5B shows the resonant frequency measured with thermal noise as a function of the tip sample separation for a series of similar triangle cantilevers. FIG. 5C shows the quality factor Q measured in a similar fashion as a function of tip-sample separation. The x-axis in all three graphs extends out to 2 mm. It is apparent that the three quantities, cantilever deflection in volts $\Delta V$ (FIG. 5A), quality factor Q (FIG. 5B) and resonant frequency $\omega_0$ (FIG. 5C) have differing dependences on tip-sample separation. This implies that $\kappa$ is a function of tip-sample separation. FIG. 6 shows $\kappa$ as a function of tip-sample separation for eleven different amplitudes, frequencies and cantilevers. These measurements imply that $\kappa$ has a predictable behavior, at least for a particular lever in the amplitude and frequency range tested in this work. The curve in FIG. 6 can then be used in conjunction with Equation 3 to predict InvOLS and, via Equation 4, the spring constant of the lever.

Figure 7:
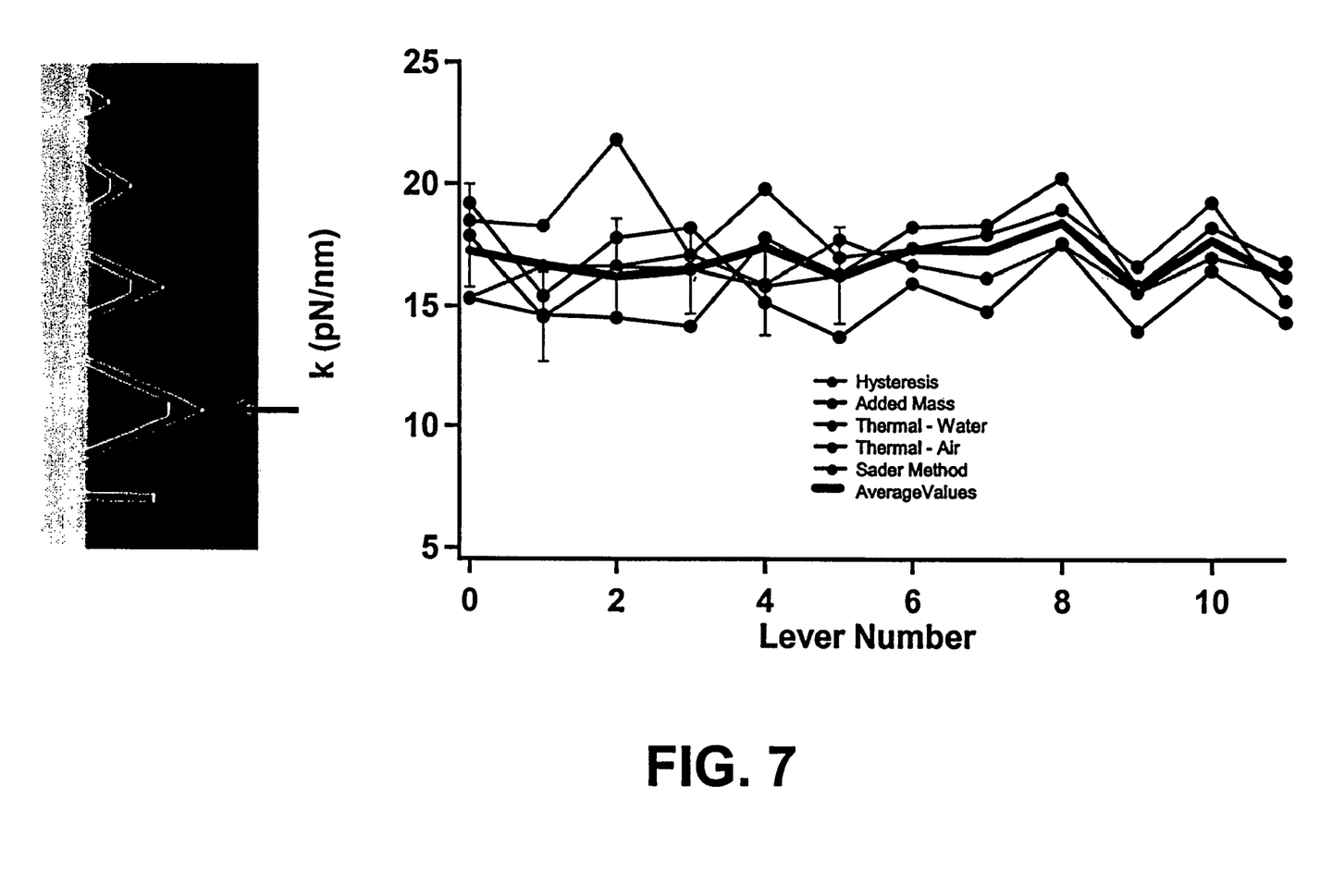
FIG. 7 depicts a graphical representation of spring constants for a of a plurality of cantilevers utilizing a plurality of different methods for calculating the spring constants, including the method according to the present invention.

FIG. 7 shows five separate calculations of cantilever spring constants for 12 different cantilevers using five different methods, including the hysteretic method disclosed here, as well as the average of all calculations. The variation is pronounced, but each method yields a result generally within 20% of any other.

Figure 8:
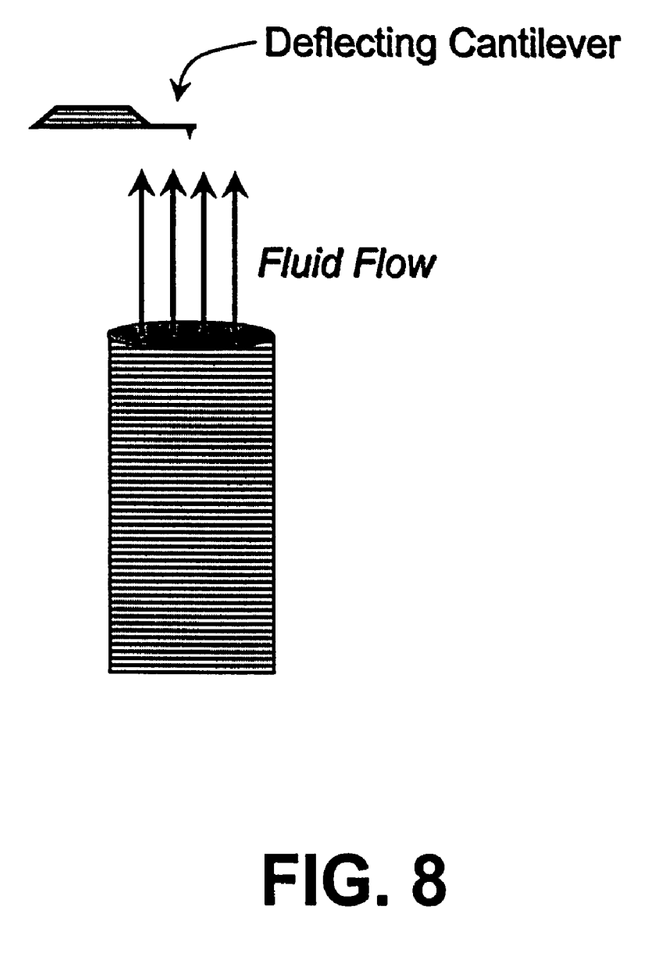
FIG. 8 depicts a simplified block diagram of an apparatus for measuring a fluid flow rate.

In one embodiment of the present invention, the fluid flow around the cantilever is induced by moving the base of the cantilever. It is also possible, and in some situations desirable, to induce fluid flow around the lever with some other method, such as an external pump or perfusion apparatus. FIG. 8 schematically illustrates such an arrangement, where the fluid flow 420 is controlled by an external apparatus to flow over the cantilever 422.

The measurement of hysteresis loops while monitoring cantilever deflection required for determining InvOLS in the disclosed method, has an additional benefit. Because the cantilever damping changes as a function of tip-sample separation (see FIG. 4 and the plotted amplitude of hysteresis in Panel A of FIG. 5) observing these hysteresis curves allows the position of the surface to be determined without actually making contact with the sample. The increasing hysteresis as the cantilever approaching the surface allows the surface to be approached to within a few microns without actually making contact. This has utility, for example, in atomic force microscopy where gently bringing the cantilever tip into proximity with the surface is a common challenge.

It is to be noted that if instead of the above situation, the spring constant and damping constant were known but the fluid flow speed was not, the drag measurement would yield a value for the fluid flow rate past the lever via the relationship $$v = -\frac{b_{hyst}}{k \cdot \Delta V \cdot InvOLS}.$$

This can be used as a probe of fluid flow as illustrated in FIG. 8.

The described embodiments of the invention are only considered to be preferred and illustrative of the inventive concept. The scope of the invention is not to be restricted to such embodiments. Various and numerous other arrangements may be devised by one skilled in the art without departing from the spirit and scope of the invention.

The invention claimed is:

1. A method of determining characteristics of a cantilever for use in cantilever-based instruments, comprising:
    measuring a drag force acting on a cantilever by monitoring a deflection of the cantilever;
    determining a power spectrum of the cantilever;
    measuring motion of a base of the cantilever; and
    determining one or more characteristics of the cantilever based on the motion of the base, the power spectrum, and the cantilever deflection.

2. The method as claimed in claim 1, including applying the drag force by directing a fluid flow over the cantilever; and
    the determining characteristics includes determining a fluid flow rate of the fluid flow.

3. The method as claimed in claim 2, wherein the determining the fluid flow rate includes determining the fluid flow rate based at least in part on a spring constant and dampening constant of the cantilever.

4. The method as claimed in claim 3, wherein applying the drag force includes oscillating the cantilever;
    the monitoring the deflection includes monitoring the deflection of the cantilever while oscillating;
    the determining characteristics includes determining a hysteresis of the deflection of the cantilever as a function of position of the base of the cantilever.

5. The method as claimed in claim 1, wherein the monitoring the deflection includes determining a hysteresis of deflection of the cantilever and monitoring the hysteresis; and
    the determining characteristics includes determining a distance between the cantilever tip and the surface.

6. The method as claimed in claim 1, wherein the applying the drag force includes oscillating the cantilever;

the monitoring the deflection includes monitoring the deflection of the cantilever while oscillating the cantilever; and the determining characteristics includes determining a spring constant based at least in part on the power spectrum associated with the cantilever.

7. The method as claimed in claim 6, wherein the monitoring the deflection further includes determining a hysteresis of deflection of the cantilever and monitoring the hysteresis; and the determining characteristics includes determining a distance between the cantilever tip and the surface based at least in part on the hysteresis.

8. The method of claim 6, wherein the monitoring the deflection further includes determining a hysteresis of deflection of the cantilever and monitoring the hysteresis; and the determining characteristics includes determining dissipation between the cantilever tip and the surface in accordance with the hysteresis of deflection of the cantilever.

* * * * *